(12) United States Patent
Muehlhoff et al.

(10) Patent No.: US 6,341,865 B1
(45) Date of Patent: Jan. 29, 2002

(54) LASER SCANNING OPHTHALMOSCOPE

(75) Inventors: Dirk Muehlhoff, Jena; Dietrich Schweitzer, Neustadt/Orla, both of (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 09/366,903

(22) Filed: Aug. 4, 1999

(30) Foreign Application Priority Data

Aug. 4, 1998 (DE) .......................................... 198 35 067

(51) Int. Cl.[7] .................................................. A61B 3/10
(52) U.S. Cl. ...................................................... 351/221
(58) Field of Search ................................ 351/205, 206, 351/209, 210, 213, 215, 220, 221; 606/4; 600/318

(56) References Cited

U.S. PATENT DOCUMENTS 4,768,873 A * 9/1988 Webb .......................... 351/205
6,099,127 A * 8/2000 Manivannan et al. ........ 351/221
6,244,712 B1 * 6/2001 Smith et al. ................. 351/221

* cited by examiner

Primary Examiner—George Manuel
(74) Attorney, Agent, or Firm—Reed Smith LLP

(57) ABSTRACT

A laser scanning ophthalmoscope with at least a first scanner, wherein a scanning movement is generated at least in a first direction, wherein the illumination of the eye is effected alternately with different wavelengths during the scanning movement in the first direction and a first image is received for a first illumination wavelength and a second image is received for a second illumination wavelength, and a plurality of images which are received in this way are compared with one another and correction values are determined from the object displacement of images received at an illumination wavelength for the images received at the other respective illumination wavelength.

10 Claims, 4 Drawing Sheets

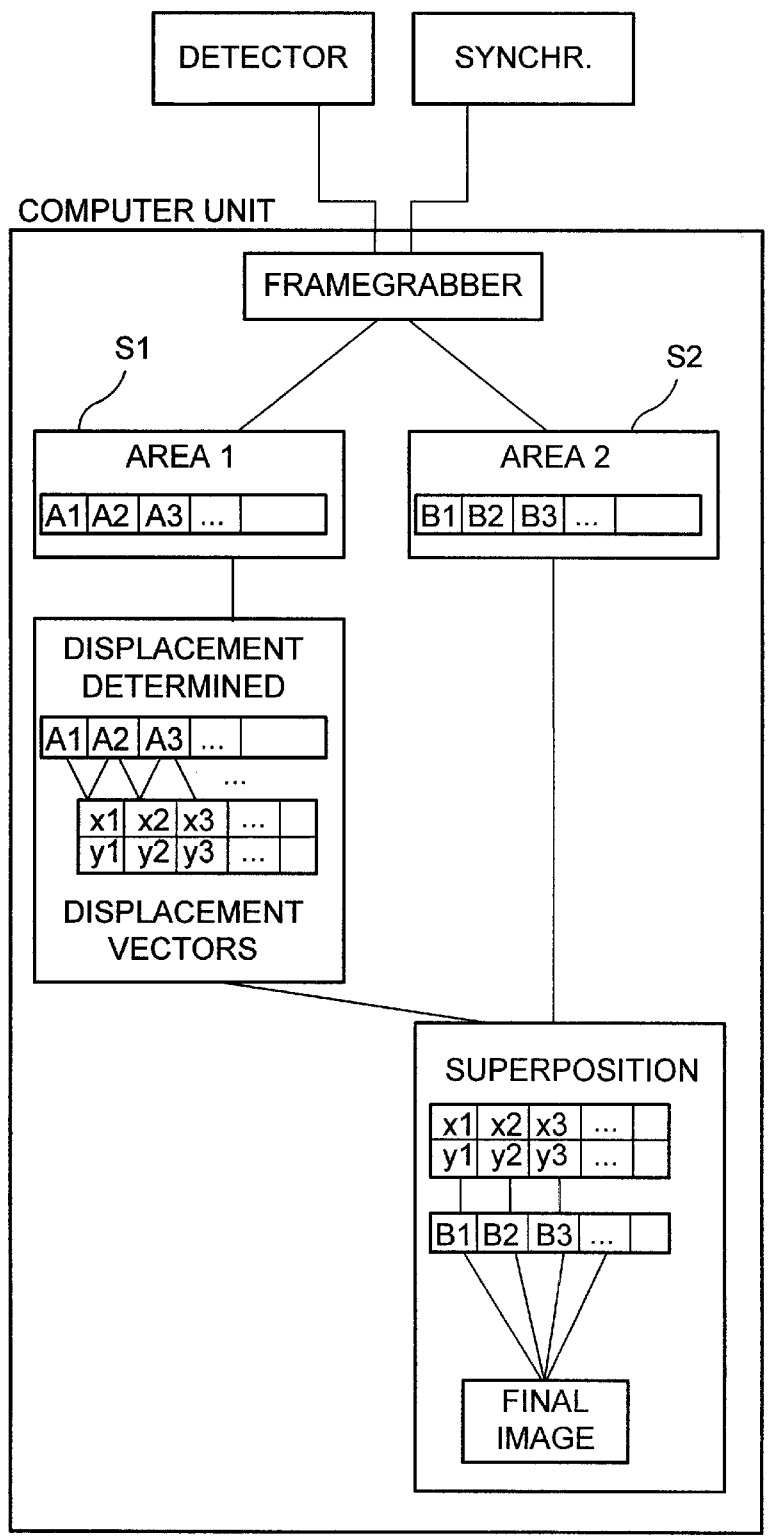
F I G. 2

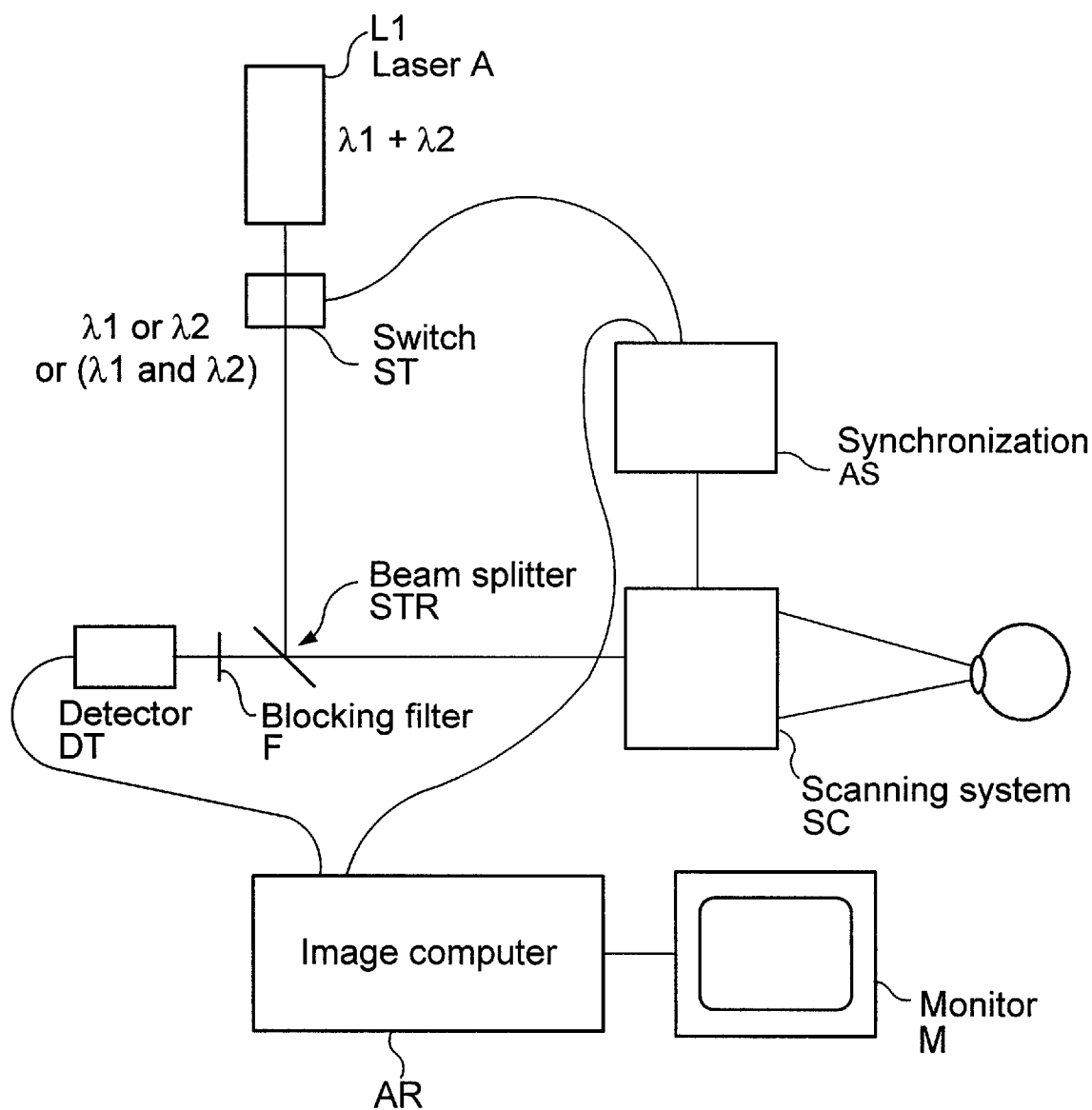
F I G. 3

LASER SCANNING OPHTHALMOSCOPE

BACKGROUND OF THE INVENTION a) Field of the Invention

The invention relates to laser scanning ophthalmoscopes which are used in clinical environments and in research to carry out fluorescence angiograms.

b) Description of the Related Art

Beyond these areas, autofluorescence has increased in importance. Formerly, there was no marketable device which enabled reliable detection of autofluorescence. The fundamental problem of autofluorescence is small signal outputs which lead to a poor signal-to-noise ratio (SNR). A known possibility for improving the SNR is by averaging over a plurality of images recorded at the same location. Since the eye of the patient is rarely stationary, movements occur between individual images which must be corrected prior to a superposition of the images. For this purpose, it is known to find prominent points in individual images, wherein displacements from one image to the other can be determined on the basis of these prominent points.

Because of the poor SNR mentioned above, individual autofluorescence images show few distinctive points, so that it is difficult to determine displacement. Known methods for finding the necessary prominent points require elaborate processing of all of the images to be superposed. This processing involves a smoothing of individual images, for example.

DE 3818084 A1 (Priority: May 27, 1987 JP P62-130832) Inventor: Akihiko Sekine

The patent describes the use of a scanning laser ophthalmoscope with two or more detectors, so that two parallel series of images can be taken into account simultaneously. An electronic arrangement is provided which allows images of one series to be superposed with images of the other series.

EP 0290566 B1 (U.S. Pat. No. 5,177,511)

A laser scanning ophthalmoscope (LSO) with a detector formed of a plurality of individual detectors is described, wherein the signal of the individual detectors is calculated to form a total signal.

OBJECT AND SUMMARY OF THE INVENTION

It is the primary object of the invention to superpose received images with poor signal-to-noise ratios without the need to find prominent points in these images themselves.

This object is met in accordance with the invention by a laser scanning ophthalmoscope with at least a first scanner, wherein a scanning movement is generated at least in a first direction, wherein the illumination of the eye is effected alternately with different wavelengths during the scanning movement in the first direction and a first image is received for a first illumination wavelength and a second image is received for a second illumination wavelength, and a plurality of images which are received in this way are compared with one another and correction values are determined from the object displacement of images received at an illumination wavelength for the images received at the other respective illumination wavelength.

In an advantageous realization of the invention, the scanning laser ophthalmoscope uses a resonance scanner as a high-speed horizontal scanner. This resonance scanner has a swiveling mirror which carries out a sinusoidal angular oscillation considered over time. A line of a first half-image is received during the forward movement of the scanner, and a line of a second half-image is received during the return movement of the scanner. With suitably fast optical switching, it is possible to activate a laser A during the forward movement in order to receive autofluorescence signals and to activate a laser B during the return movement in order to receive reflection signals. Accordingly, it is possible to record two different images or series of images $B_A$, $B_B$ which coincide.

Discrepancies between the images lie within the order of magnitude of a line spacing and are accordingly insignificant with respect to further processing.

The described images differ with respect to signal characteristics. While structures are barely detectable, if at all, in an individual autofluorescence image, structures can be detected in a reflection image due to the much improved signal gain.

Alternatively, rather than switching the lasers, it is possible to arrange a high-speed switchable filter (e.g., AOTF) in front of the detector and to switch this filter in such a way that a fluorescence signal or a reflection signal is included in alternate lines.

Displacements from one image to the next (for purposes of movement corrections for the superposition of autofluorescence images) can therefore be determined on the basis of low-noise, simultaneously recorded reflection images. Since the two images are received almost simultaneously, the displacements between two reflection images are identical to the displacements between two autofluorescence images. Accordingly, it is possible to correct displacements between two autofluorescence images without this displacement being determined on the basis of the autofluorescence images themselves.

Alternately, it is also possible for a reflection image to be received not only almost simultaneously, but fully simultaneously in that the reflection signal is obtained by a second detector. The second detector lies parallel to the first and is only outfitted with a different filter combination.

The invention is described more fully hereinafter with reference to the schematic drawings.

BRIEF DESCRIPTION OF THE INVENTION

In the drawings:

FIG. 2 shows the correction process according to the invention;

FIG. 3 shows a first arrangement according to the invention; and

DESCRIPTION OF THE PREFERRED EMBODIMENTS

Figure 1:
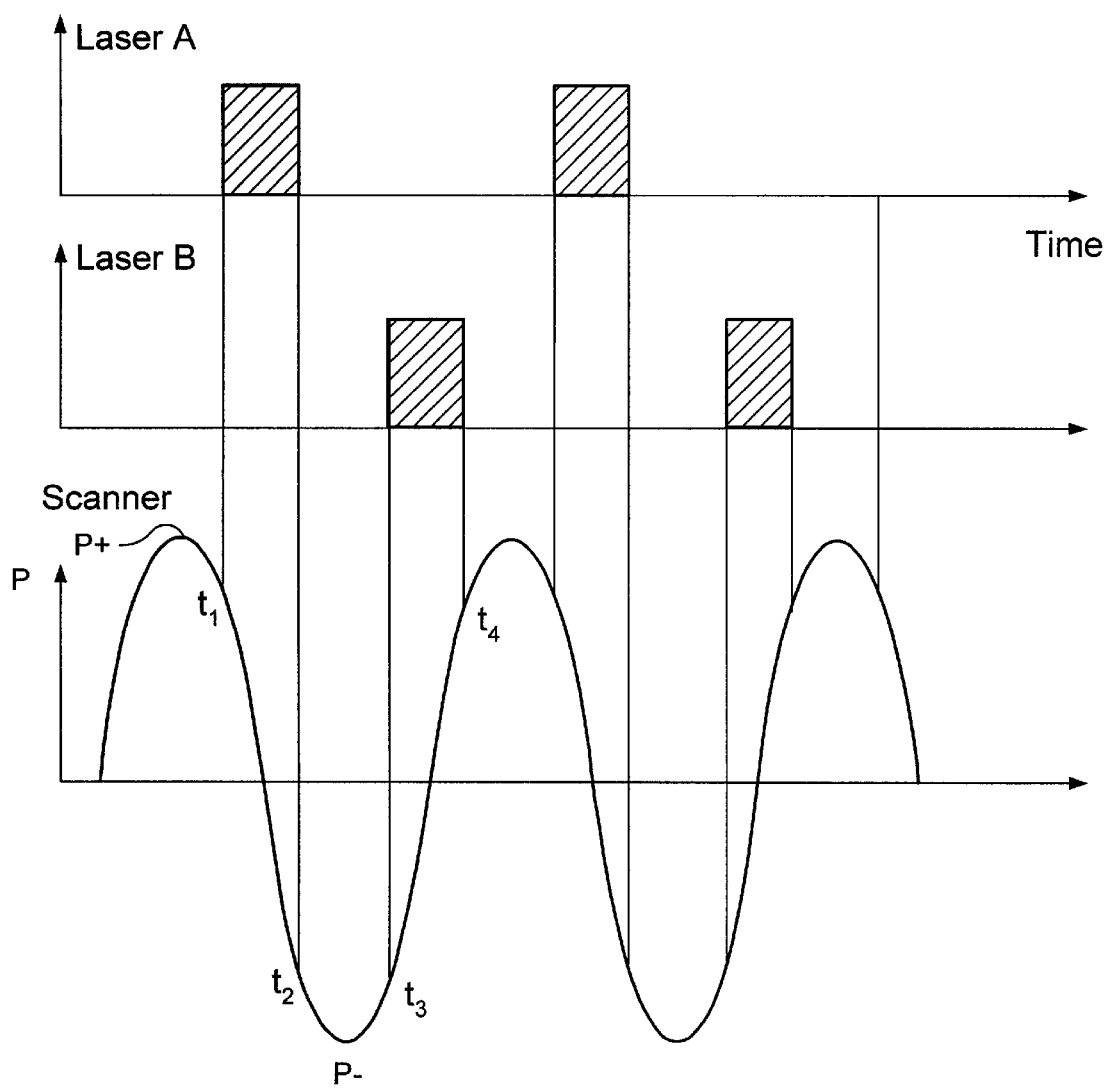
FIG. 1 shows the switching of two lasers in accordance with the invention.

FIG. 1 shows the oscillation curve of a resonance scanner over time which shows the position P of the swiveling mirror about a point 0 (center position).

In a time period t1–t2 corresponding to a swiveling movement of the mirror in one direction, in this case, from P+ in the direction of P–, a first laser A is switched on for illumination of the fundus oculi. A second laser B is switched on in time period t3–t4 when swiveling back from P– in the direction of P+.

The vertical scanner does not change its position at all between t1 and t4, or, if so, then only insignificantly, so that laser A sweeps over essentially the same scanning line on the fundus oculi in the forward direction as laser B in the return direction. Laser B, with a wavelength of, e.g., $\lambda B=488$ nm, serves to generate fluorescence signals and laser A, with a wavelength of, e.g., $\lambda A=780$ nm, serves to generate reflection signals.

FIG. 2 shows the correction process. The half-images A1, A2 . . . and B1, B2 which are received during illumination by lasers A and B, wherein half-images B1, B2 correspond to a plurality of scans of the same image area, are synchronized, digitized and deposited via a framegrabber in storage areas S1 and S2. Based on characteristic image features x1, x2 in A1, y1, y2 in A2, etc., a plurality of reflection images A are compared with one another in storage S1 and the image displacement is determined based on image displacement vectors (x1, y1) . . . This image displacement is now used as a correction in order to superpose the received individual fluorescence images B1, B2 in S2 and to combine them to form a final image.

FIG. 3 shows a laser L1 which has two wavelength ranges $\lambda 1 \lambda 2$. The laser L1 can be an argon ion laser with wavelengths 488 nm and 514 nm. This laser can be switched between wavelengths by means of a switch ST, for example, an AOTF. The switching of the switch ST is synchronized with the scanning system SC and the movement of the horizontal mirror via a control unit AS. Detection is carried out via a beam splitter STR and filter F by means of a detector DT which is connected with an evaluating computer AR in which the correction process described with reference to FIG. 2 is carried out, and the corrected image is displayed on a monitor M.

Figure 4:
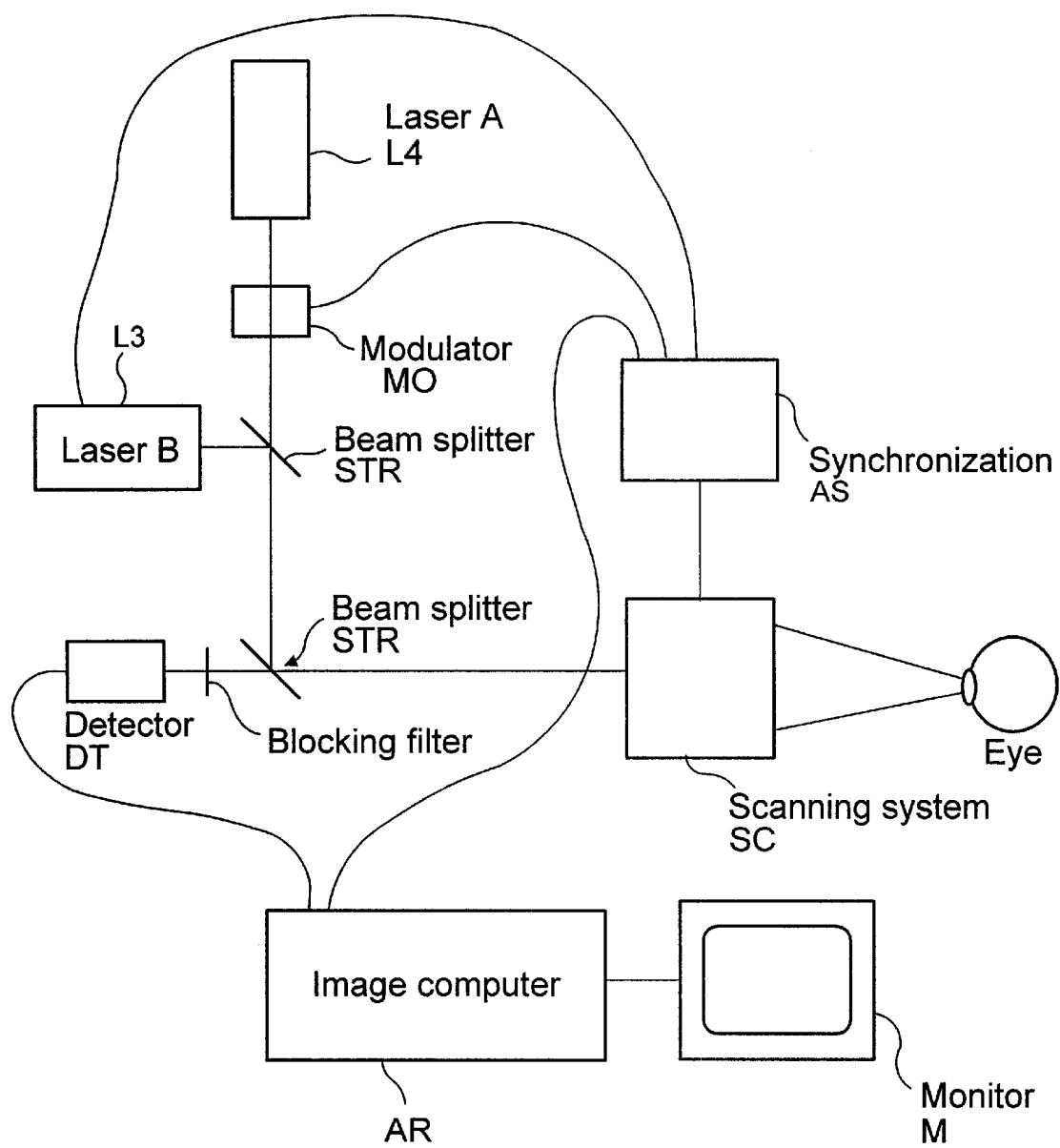
FIG. 4 shows a second arrangement according to the invention.

For this purpose, the filter F is so configured with respect to its spectral characteristics that it transmits fluorescence radiation excited by $\lambda 1$ and the occurring reflected light of wavelength $\lambda 2$. However, the radiation of wavelength $\lambda 1$ which is reflected by the eye is not transmitted. Different lasers L3 and L4 are provided in FIG. 4 for generating a reflection image and a fluorescence image which are coupled into the illumination beam path via beam splitters.

In this arrangement, the laser L3 with wavelength $\lambda 3$ for fluorescence excitation which is not transmitted by the filter is operated in an unmodulated manner, i.e., in CW mode. Laser L4 with wavelength $\lambda 4$ which is transmitted by the filter is modulated with modulator MO. The modulator switches the laser L4 in every second line or only in the forward or return run of the scanner. Therefore, two lines with different image information occur alternately. The storage areas described by this information contain images containing reflection information and fluorescence information, e.g., in area S2. Due to the fact that the fluorescence signals are substantially weaker than the reflection signals, the fluorescence contributions are not troublesome. The image processing is carried out in the same way as described above.

The embodiments described above can also be transferred to a scanner principle which does not work by swinging back and forth. A unidirectional scanning principle like that of a polygon scanner can also be used. For this purpose, the line scanning processes are numbered. The switching of the laser sources is carried out in the same way as when a bidirectional scanner is used, wherein, in this case, all odd lines are identified with the forward swing and all even lines are identified with the return swing.

While the foregoing description and drawings represent the preferred embodiments of the present invention, it will be obvious to those skilled in the art that various changes and modifications may be made therein without departing from the true spirit and scope of the present invention.

What is claimed is:

1. A laser scanning ophthalmoscope comprising:

at least a first scanner, wherein a scanning movement is generated at least in a first direction, wherein the illumination of the eye is effected alternately with different wavelengths during the scanning movement in the first direction and a first image is received for a first illumination wavelength and a second image is received for a second illumination wavelength; and means for comparing a plurality of images which are received in this way with one another and for determining correction values from the object displacement of images received at an illumination wavelength for the images received at the other respective illumination wavelength.

2. The laser scanning ophthalmoscope according to claim 1, wherein a laser with a plurality of wavelengths is used, and wherein an optical switch which is synchronized with the scanning system switches the wavelengths of the laser.

3. The laser scanning ophthalmoscope according to claim 1, wherein two lasers with different illumination wavelengths are provided for image generation.

4. The laser scanning ophthalmoscope according to claim 1, wherein two lasers are provided, wherein one laser is continuously active and the second laser is active only during the forward scanning movement or reverse scanning movement or during every second scanning movement.

5. The laser scanning ophthalmoscope according to claim 4, wherein the light of the continuously active laser is blocked by a filter in front of the light receiver, and wherein this filter transmits the light of the second laser.

6. A laser scanning ophthalmoscope comprising:

at least a first scanner, wherein a scanning movement is generated in a first direction and in a return direction, wherein the illumination of the eye is carried out during the scanning movement in the first direction with a different wavelength than in the return direction and a first image is received for the first direction and a second image is received for the return direction; and means for comparing a plurality of images received in the first direction or in the return direction with one another and for determining correction values from the object displacement for the images received in the other respective direction.

7. The laser scanning ophthalmoscope according to claim 6, wherein a laser with a plurality of wavelengths is used, and wherein an optical switch which is synchronized with the scanning system switches the wavelengths of the laser.

8. The laser scanning ophthalmoscope according to claim 6, wherein two lasers with different illumination wavelengths are provided for image generation.

9. The laser scanning ophthalmoscope according to claim 6, wherein two lasers are provided, wherein one laser is continuously active and the second laser is active only during the forward scanning movement or reverse scanning movement or during every second scanning movement.

10. The laser scanning ophthalmoscope according to claim 6, wherein the light of the continuously active laser is blocked by a filter in front of the light receiver, and wherein this filter transmits the light of the second laser.

* * * * *